Figure 4:
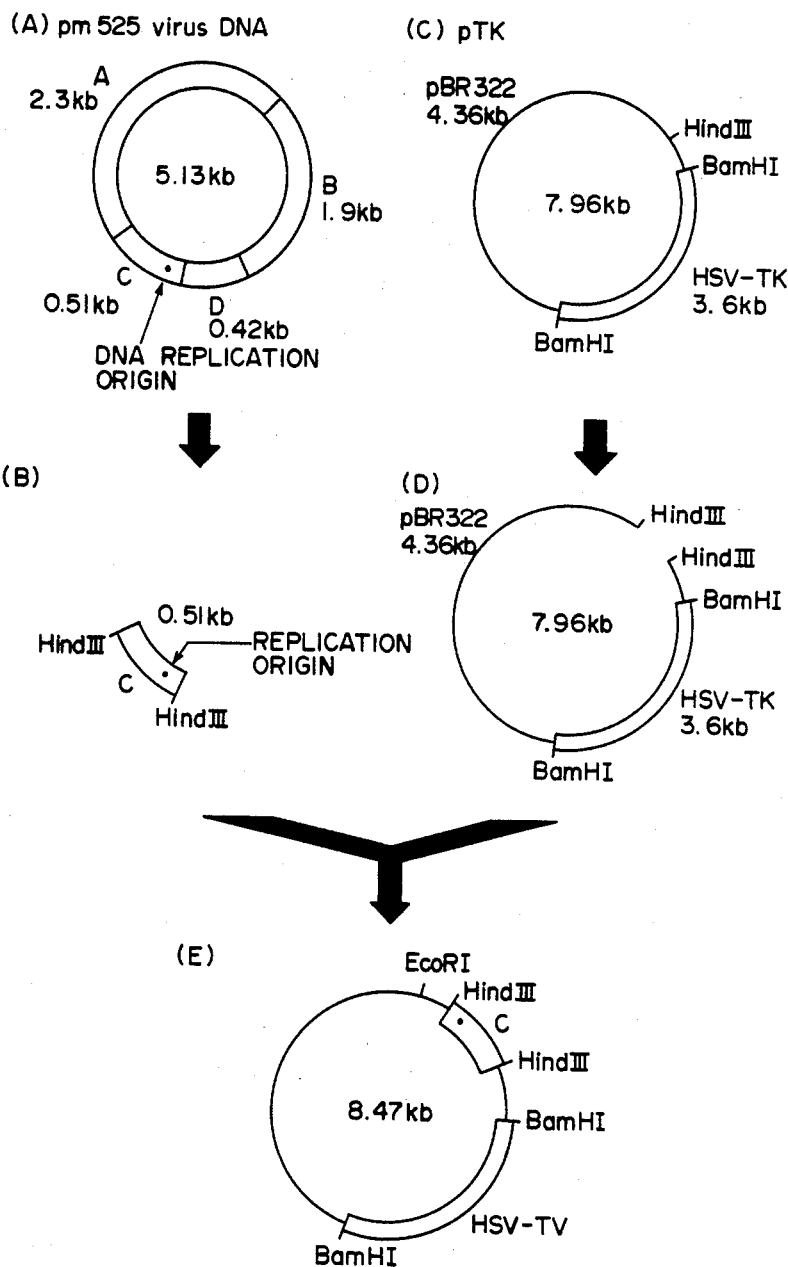

United States Patent [19]

Soeda et al.

[11] Patent Number: 4,722,897
[45] Date of Patent: Feb. 2, 1988

[54] VIRAL ENHANCER DNA SEGMENTS

[75] Inventors: Eiichi Soeda, Mishima; Hiromitsu Yoshimura, Hasuda, both of Japan

[73] Assignee: Taisho Pharmaceutical Co., Ltd., Tokyo, Japan

[21] Appl. No.: 709,281

[22] Filed: Mar. 7, 1985

[30] Foreign Application Priority Data

Mar. 8, 1984 [JP] Japan .................................. 59-44437

[51] Int. Cl.$^4$ ...................... C12P 21/00; C12N 15/00; C07H 15/12
[52] U.S. Cl. .................................. 435/68; 435/172.3; 435/172.1; 536/27; 935/36
[58] Field of Search ........................ 435/172.3, 68, 71; 536/27; 935/8, 7, 36

[56] References Cited

PUBLICATIONS

Watanabe et al, Journal of Virology, vol. 42, pp. 978–985, Jun. 1982.
Khoury et al, Cell, vol. 33, pp. 313+314, Jun. 1983.

Primary Examiner—Alvin E. Tanenholtz
Attorney, Agent, or Firm—Wenderoth, Lind & Ponack

[57] ABSTRACT

An enhancer DNA segment having an excellent action of enhancing the transcriptional efficiency of an incorporated gene in a cell, said segment being derived from a human papovavirus BK mutant designated as pm411, pm522 or pm525.

The enhancer DNA segment is useful for enhancing the expression of a gene encoding a biologically active substance in host eukaryotic cells.

5 Claims, 8 Drawing Figures pm 411 HindIII-C

5'—AGCTTGTGTCGTGACAGCTGGGCGCAGAACCATGGCCTTTGTCCAGTTTAACTATTAACTGCCACTGGCT
GGCTGCCCAGTCATGCACTTTCCTTCCTGAGGTCACTTTCCTTCCTGAGGTCATGCACTTTCCTTCCTGA
GGGCTGCCCAGTCATGCTGAGGTCTGGCTGCCCAGTCATGCACTTTCCTTCCTGAGGGCTGCCCA
GTCATGCACTTTCCTTCCTGAGGTCATGGTTTGGCTGCATTCCATGGGTAAGCAGCTCCTCCCTGTGGCC
TTTTTTTTATAATATATAAGAGGCCGAGGCCGGCCTCTGCCTCCACCCTTTCTCTCAAGTAGTAAGGGTG
TGGAGGCTTTTTCTGAGGCCTAGCAAAACTATTTGGGGAAATCCCTATTCTTTTGCAATTTTTGCAAAAA
TGGATAAAGTTCTTAACAGGGAAGAATCCATGGAGCTCATGGACCTTTTAGGCCTTGAAAGAGCTGCCTG
GGGAAATCTTCCCTTAATGAGAAA.

Fig. 1 pm 522   HindIII-C
                                    HaeII
5'---AGCTTGTGTCGTGACAGCTGGGCGCAGAACCATGG|CCTTTGTCCAGTTTAACTATTAACTGCCACTGGCT
GGCTGCCCAGTCATGCACTTTCCTTCCTGAGGTCATGGCTGCCCAGTCATGCACTTTCCTTCCTGA
GGGCTGCCCAGTCATGCACTTTCCTTCCTGAGGTCATGGTTTGGCTGCATTCCATGGGTAAGCAGCTCCT
CCCTGTGG|CCTTTTTTTTATAATATATAAGAGGCCGAGGCCGCCTCTGCCTCCACCCTTTCTCTCAAGT
         HaeIII                           HaeIII
AGTAAGGGTGTGGAGGCTTTTCTGAGGCCTAGCAAAACTATTTGGGGAAATCCCTATTCTTTTGCAATT
                          HaeIII
TTTGCAAAAATGGATAAAGTTCTTAACAGGGAAGAATCCATGGAGCTCATGGACCTTTTAGGCCTTGAAA
                                                              HaeII
GAGCTGCCTGGGGAAATCTTCCCTTAATGAGAAA.

Fig. 2 pm 525 HindIII-C

5'---AGCTTGTCGTGACAGCTGGCGCAGAACCATGG|CCTTTGTCCAGTTTAACTATTAACTGCCACTGGCT
                                    HaeIII
GGCTGCCCAGTCATGCACTTTCCTTCCTGAGGTCATGGCTGCGCCCAGTCATGCACTTTCCTTTGTCC
AGTTTAACTATTAACTGCCACTGGCTGGCTGCCCTAGTCATGCACTTTCCTTCCTGAGGGCTGCCTAGTC
ATGCACTTTCCTTCCTGAGGTCATGGTTTGGCTGCATTCCATGGGTAAGCAGCTCCTCCCTGTGG|CCTTT
                                                                 HaeIII
TTTTTTATAATATATAAGAGG CCGAGG CCGCCTCTGCCTCCACCCTTTCTCTCAAGTAGTAAGGGTGTGG
              HaeIII  HaeIII
AGGCTTTTTCTGAGG CCTAGCAAAACTATTTGGGGAAATCCCTATTCTTTTGCAATTCTTTGCAAAAATGG
          HaeIII
ATAAAGTTCTTAACAGGGAAGAATCCATGGAGCTCATGGACCTTTTAGGCCTTGAAAGAGCTGCCTGGGG
                                                         HaeIII
AAATCTTCCCTTAATGAGAAA.

Fig. 3

Fig. 5
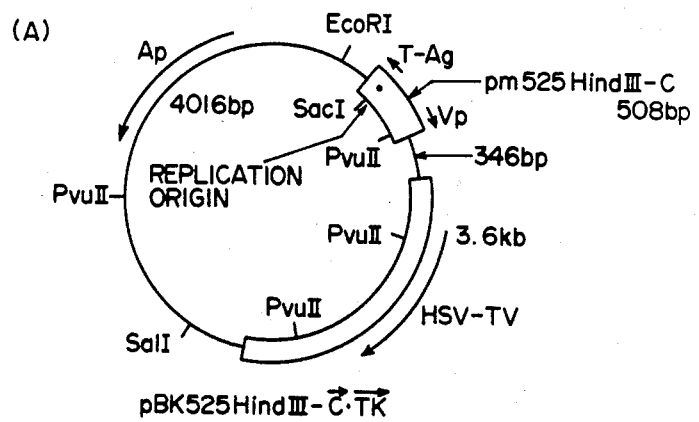
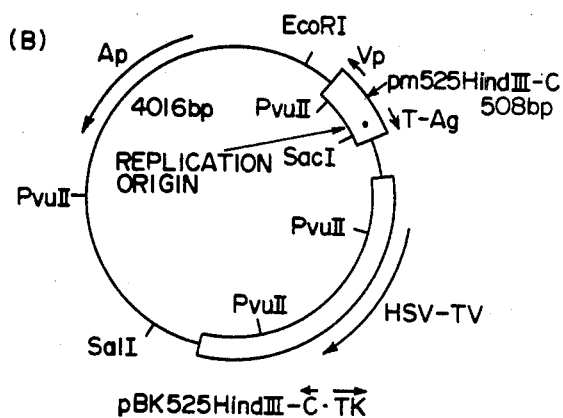
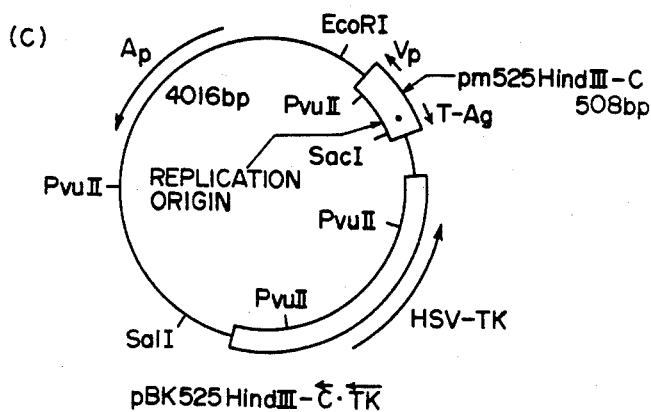

Fig. 6
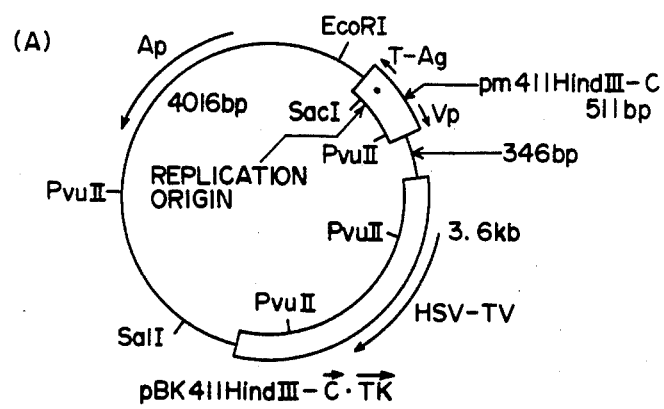
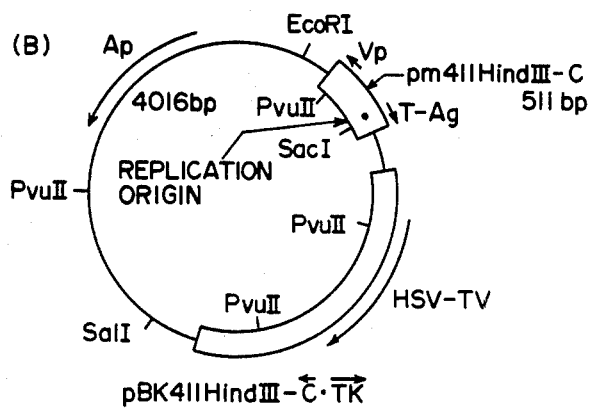
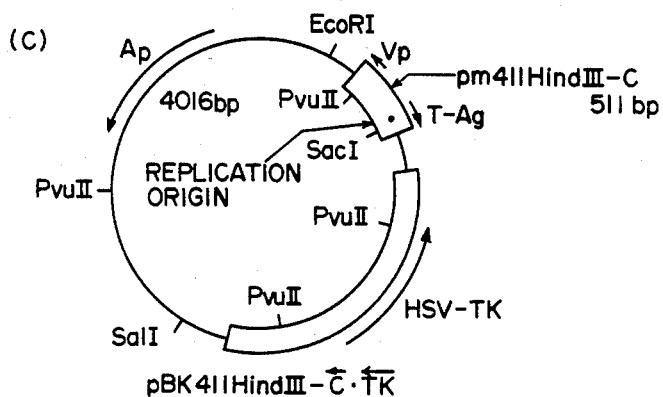

Fig. 7
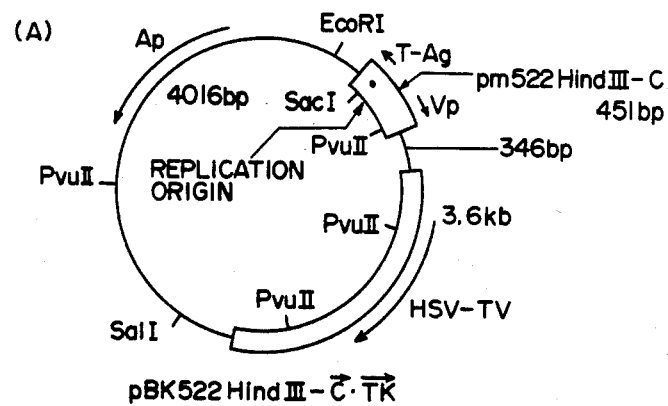
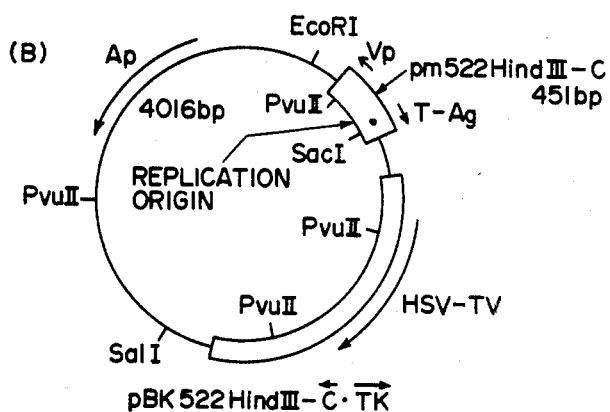
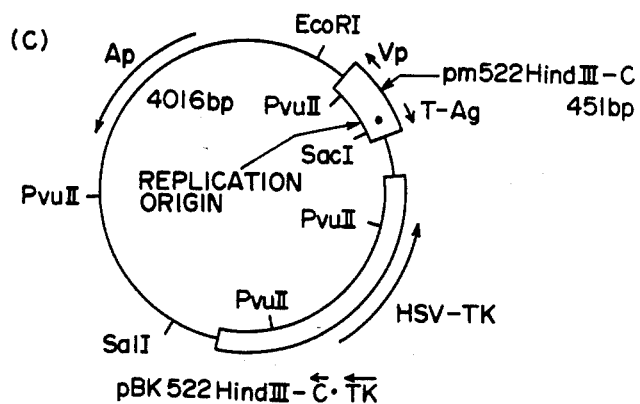

VIRAL ENHANCER DNA SEGMENTS

This invention relates to viral enhancer DNA segments, and more specifically, to enhancer DNA segments derived from certain human papovavirus mutants and having an excellent action of enhancing the transcriptional efficiency of an incorporated gene in a cell.

Recently, a DNA region required for transcription of a gene attracted interest in the course of studies on gene expression. Chambon (Nature, 290, 304, 1981; Proc. Natl. Acad. Sci., USA, 77, 3898, 1980) and Shaffner (Cell, 27, 299, 1981; Nucl. Acid Res., 9, 6251, 1981) analyzed the action of a DNA fragment near the promoter of a viral DNA separated from Simian virus 40 or mouse polyoma virus, and showed that when such DNA fragment is linked to another gene, the transcriptional efficiency of the other gene is markedly enhanced. This DNA fragment was named an "enhancer" since its effect appears independently of the orientation of linking, the distance from a gene to which it is linked, and the type of the other gene.

Very recently, Rosenthal et al. (SCIENCE, 222, 749, 1983) reported that the repeated region near the origin of DNA replication of the Dunlop strain of human papovavirus BK (to be abbreviated BKV) has an enhancer function. Watanabe et al. (J. Virol., 42, 978, 1982) also reported that characterization of recombinant DNAs constructed from a wild type BKV DNA fragment lacking HindIII-C segment and the HindIII-C segment of DNA of the turbid-plaque-forming mutant (pm522) of BKV showed that the change of DNA occurring near the origin of replication, somewhere within HindIII-C, enhances the transforming capability. Watanabe et al., however, did not refer to the enhanced activitY of genes (or heterologous genes) capable of producing biologically active substances, the determination of the presence of an enhancer DNA segment, nor to the determination of its nucleotide sequence by cloning.

The present inventors have now succeeded in isolating enhancer DNAs from the HindIII-C fragments of DNAs of BKV mutants pm411, pm522 and pm525 strains, and in determining their nucleotide sequences. The present inventors have introduced such an enhancer DNA into a vector containing a gene which codes for a biologically active substance (to be referred to as the "target gene"), transforming the cells of a certain animal with the recombinant DNA, and examined the transcriptional efficiency of the target gene. This examination has led to the discovery that the enhancer DNA increases the transcriptional efficiency of the target gene to several tens of times and markedly increases the production of the biologically active substance and that its action to enhance the transcriptional efficiency is several times as high as that of an enhancer DNA obtained from a DNA of wild type BKV (prototype BKD).

Accordingly, the enhancer DNA segments provided by this invention are of great importance in producing various useful biologically active substances, particularly proteinous biologically active substances such as modified proteins and various lymphokines typified by glycosilated γ-interferon and interleukin II by gene technology utilizing eukaryotic cells.

In spite of the noteworthy advance in recombinant DNA technology, the production thereby of such eukaryotic proteins, in many cases, has had to be carried out in prokaryotic host cells because the growth of the eukaroytic cells is slow, and the expression efficiency of genes introduced into them is low. However, with proteins having a carbohydrate portion, the prokaryotes do not have the function of correctly binding their carbohydrate portion to proteins. Thus, proteins modified with such a carbohydrate portion cannot be produced in prokaryotic cells by the recombinant DNA technology.

The use of eukaryotic cells, therefore, is essential to the production of modified biologically active proteins by the recombinant DNA technology. The eukaryotic cells, however, have a much longer generation altenation time than prokaryotic cells and are unsuitable for commercial production of the desired biologically active substances.

The enhancer DNA segments provided by this invention offer a solution to the above problem in the production of biologically active substances by utilizing eukaryotic cells. Specifically, when the eukaryotic cells are transformed with a recombinant DNA having the enhancer DNA segment of this invention inserted thereinto together with a gene capable of producing the biologically active substances (the target gene), the production of the desired biologically active substance increases to several tens of times as large as in the case of transforming the eukaryotic cells with a recombinant DNA having only the target gene inserted thereinto.

The enhancer DNA segments provided by this invention are DNAs obtained by digesting the HindIII-C fragments of BKV mutants, pm411, pm522 and pm525, with the restriction endonuclease HaeIII and having a size of 243 bp (pm411), 183 bp (pm522) and 240 bp (pm525), respectively, and have the nucleotide sequences shown in FIGS. 1 to 3. The nucleotide sequences shown in FIGS. 1 to 3 are those of the entire HindIII-C fragments, and the nucleotide sequences of the enhancer DNA portions are surrounded by dotted lines. The underlined part of the enhancer DNA sequences is common to the nucleotide sequences of the enhancer DNAs of all three mutants mentioned above.

The enhancer DNA segments provided by this invention have the following characteristics.

(1) They have relatively short nucleotide sequences suitable for gene manipulation.

(2) They exhibit an action of enhancing the level of transcription independently of the orientation of linking to the target gene. In other words, they can increase transcriptional efficiency in a manner relatively independent of orientation with respect to a gene.

(3) They act also on a distant gene and keep activity even when incorporated at a position upstream or downstream of that gene.

(4) They enhance the transcriptional efficiency independently of the type of the target gene.

(5) They exhibit an action of enhancing transcriptional efficiency on any type of eukaryotic host cells.

The enhancer DNA segment of this invention is derived from pm 411, pm522 or pm525, all of which are mutants of BKV, and can be obtained, for example, by digesting the DNA of pm411, pm522 or pm525 with the restriction endonuclease HindIII, and further digesting the resultant HindIII-c fragment with the restriction endonuclease HaeIII. More specifically, the DNA fragment having an activity of enhancing transcriptional efficiency can be obtained by extracting a viral DNA from each of the aforesaid mutants of BKV (distributed by Department of Enteroviruses, National Institute of Health located at Kamiosaki, Shinagawa-ku, Tokyo, Japan), purifying it, digesting the viral DNA with HindIII, isolating the HindIII fragment, linking it to TK gene (the TK gene of herpes simplex virus-Type I virus DNA inserted into pBR322) to construct a recombinant plasmid DNA, transfecting eukaryotic cells (such as F2408 TK⁻ cells derived from rat or LTK⁻ cells derived from mouse) with the recombinant plasmid DNA by the calcium phosphate method to form transformants, cultivating the transformants in HAT medium, and measuring the number of colonies formed to determine the transcriptional enhancing activity. By extracting DNA from the transformants, again digesting the DNA with HindIII, the DNA fragment can be recovered. The final product has been determined to be a HindIII-C fragment by electrophoresis.

The enhancer DNA segment in accordance with this invention can be isolated by further digesting the resulting HindIII-C fragment with HaeIII, isolating the cleavage fragments, and selecting fragments having enhancer activity by the same procedure as above.

The nucleotide sequences of the HindIII-C fragment and the enhancer DNA segment can be determined by cloning each of such fragments into mp8 phage DNA, transfecting $E.\ coli$ JM101 with the resulting vector to form a template single-stranded DNA, and applying the dideoxy method (Sanger, F., Nicklen, S. & Coulson, A. R., Proc. Natl. Acad. Sci. USA, 74, 5463, 1977) (see FIGS. 1 to 3).

The enhancer DNA segments of this invention have an action of markedly enhancing expression of an incorporated gene in a cell, namely its transcriptional efficiency. For example, as will be clear from Examples given hereinafter, the enhancer DNA segments of the invention show about 10 to about 20 times as high transcriptional enhancing activity as incorporated genes free from the enhancer DNA segment of this invention in a transcriptional enhancing activity test using mouse LTK⁻ cells.

It has been found as is clear from FIGS. 1 to 3 that the enhancer DNA segments of this invention have different nucleotide sequences depending upon the types of DNAs from which they are derived and also have different degrees of affinity for host cells (namely have different transcriptional enhancing activities depending upon the types of host cells into which they are introduced). This suggests that the enhancer DNA segments of this invention can be selected depending upon eukaroytic host cells suitable for expression of the target genes.

Conventional enhancer DNAs from monkey SV40 and mouse polyoma virus show a particularly high activity of increasing transcriptional efficiency in the monkey and mouse cells as original hosts (Nucl. Acid Res., 10, 7965, 1982). This fact fully suggests that the enhancer DNA segments of this invention prepared from human BKV will exhibit their strongest activity in human cells.

The enhancer DNA segments of this invention have relatively short base sequences suitable for gene manipulation, act only when linked to target genes, and exhibit their enhancing activity independently of the position and direction with respect to the target gene. The most suitable enhancer DNA can be selected from them for a particular eukaryotic host cells suitable for expression of a certain target gene. These enhancer nucleotide sequences are quite useful in gene technology.

The following Examples illustrate the enhancer DNA segments of this invention more specifically.

EXAMPLE 1

(1) Extraction of DNA from BK virus

Proteinase and EDTA were added to $8 \times 10^{12}$ pm525 viral particles grown in human embryonic kidney (HEK) cells so that they respectively attained a final concentration of 0.1 mg/ml and 10 mM (the final amount of the liquid 0.4 ml). The suspension was left to stand overnight at 36° C., and then well mixed with 0.4 ml of phenol. The mixture was centrifuged at 12,000 rpm for 3 minutes. The supernatant was transferred to a tube. Chloroform (0.4 ml) was added and well mixed with the supernatant, and the mixture was centrifuged at 12,000 rpm for 3 minutes. The supernatant was transferred to another tube, and 40 microliters of 3M sodium acetate and further 0.8 ml of cold ethanol were added and mixed. The mixture was left to stand at −20° C. for 4 hours, and centrifuged at 12,000 rpm for 5 minutes. The supernatant was completely removed. By the above procedure, about 40 micrograms of pm525 virus DNA was obtained [FIG. 4 (A)]. In the following experiments, this pm525 viral DNA was used as a solution in distilled water or TE buffer (10 mM Tris HCl, pH 8.0, 1 mM EDTA).

By the same method, viral DNAs were extracted from pm411 and pm522.

(2) Isolation of HindIII-C DNA fragment from BK viral DNA

Five micrograms of the DNA extracted from pm525 virus was reacted with 5 units (5 U) of HindIII (a product of Takara Shuzo Co., Ltd.) at 37° C. for 2 hours in 100 microliters of a reaction buffer (10 mM Tris HCl, pH 7.5, 60 mM NaCl, 6 mM $MgCl_2$, 1 mM dithiothreitol), and the reaction product was subjected to electrophoresis on 1% low-melting agarose gel (containing 0.5 microgram/ml of ethidium bromide) at 50 mA for about 3 hours. By UV irradiation in a darkroom, the presence of four bands was determined. The DNA fragments on these bands were named HindIII-A, B, C and D fragments from the cathode side in order of decreasing molecular sizes. The gel portion containing only the HindIII-C DNA fragment was sliced and heated at 65° C. to melt the agarose. Then, 100 microliters of TE buffer was added, and the mixture was fully mixed with phenol saturated with TE buffer. The mixture was centrifuged at 12,000 rpm for 3 minutes. The upper aqueous layer was transferred into another tube, and subjected to the phenol treatment twice. To the aqueous layer transferred to still another tube was added 3M sodium acetate in an amount one-tenth of the volume of the aqueous layer. Furthermore, a twofold amount of ethanol was added, and mixed. The mixture was left to stand at −20° C. for 4 hours, and then centrifuged at 12,000 rpm for 5 minutes. The supernatant was removed, and 100 microliters of 80% cold ethanol was gently added. The mixture was centrifuged at 12,000 rpm for 3 minutes. The supernatant was removed as much as possible, and the precipitate (DNA) was dissolved in 10 microliters of distilled water.

By the above procedure, about 0.4 microgram of the HindIII-C DNA fragment of pm525 virus (pm525 HindIII-C) was obtained [FIG. 4, (B)].

By quite the same procedure as above, the HindIII-C DNA fragments (pm411 HindIII-C and pm522 HindIII-C) were obtained from pm411 and pm522 viral DNAs.

(3) Determination of the nucleotide sequences of the HindIII-C DNA fragments of BK viral DNAs (3-1) Cloning of HindIII-C DNA fragment into mp8 phage DNA and preparation of template single-stranded DNA The pm525 HindIII-C DNA fragment (50 ng) was reacted with 2 ng of HindIII-cleaved double-stranded mp8 phage DNA (a cloning kit made by Amersham Company) at 14° C. for 3 hours in 10 microliters of a reaction buffer (50 mM Tris HCl, pH 7.5, 20 mM $MgCl_2$, 1 mM ATP, 5 mM dithiothreitol) using one unit of T4 DNA ligase (a product of Takara Shuzo Co., Ltd.). This reaction gave a recombinant DNA with the insertion of the HindIII-C DNA fragments into the HindIII site of mp8 phage DNA. The recombinant DNA was then mixed in the presence of $Ca^{2+}$ with $Ca^{2+}$-treated E. coli JM101 obtained by the calcium chloride method (T. Maniatis, E. F. Fritsch and J. Sambrook: Molecular Cloning, p. 250, Cold Spring Harbour Lab., 1982) to transform the E. coli JM101. The resulting transformants were mixed with 25 microliters of 5-bromo-4-chloro-3-indolyl-beta-galactoside (dissolved in dimethylformamide in a concentration of 20 mg/ml), 25 microliters of isopropyl-beta-D-thio-galactopyranoside (25 mg/ml, $H_2O$) and 200 microliters of E. coli JM101 in its log phase of growth, and further the mixture was well mixed with 3 ml of H top agar kept at 50° C. (tryptone 10 g, NaCl 8 g, agarose 6 g/liter). The mixture was plated on H agar plates (tryptone 10 g, NaCl 8 g, agar 12 g/liter). On overnight cultivation, blue plaques and colorless plaques formed. The colorless plaque containing the phage DNA having the pm525 HindIII-C DNA fragment inserted into it was sucked by a sterilized pipette, and inoculated in 1.5 ml of a culture fluid [obtained by diluting an overnight culture of E. coli JM101 to 100 times with 2 x TY (bacto-tryptone 8 g, yeast extract 5 g, NaCl 2.5 g/liter)]. When it was cultivated with shaking at 37° C. for 4 to 5 hours, a template single-stranded DNA emerged into the culture fluid. The culture fluid was transferred to a microcentrifuge tube, and centrifuged at 12,000 rpm for 3 minutes. Then, only the supernatant was taken into a microcentrifuge tube by means of a pipette and mixed with 200 microliters of PEG/NaCl solution (an aqueous solution containing 20% of polyethylene glycol 6000 and 2.5 M NaCl). The mixture was left to stand at room temperature for 15 minutes, and then centrifuged at 12,000 rpm for 5 minutes to precipitate the desired DNA. The supernatant was removed as much as possible. The DNA was purified by phenol treatment and ethanol precipitation in the same way as in Example 1, and dissolved in 50 microliters of TE buffer. The template single-stranded DNA prepared as above contained the HindIII-C DNA fragment of pm525 viral DNA inserted into it.

(3-2) Determination of the nucleotide sequence

By using the templete single-stranded DNA prepared in (3-1), the nucleotide sequence of Pm525 HindIII-C was examined. For the nucleotide sequence determination, the kit for determination of nucleotide sequences made by Amersham International Inc. and the attached handbook (M13 Cloning and Sequencing Handbook) were used.

First, 5 microliters of the prepared template single-stranded DNA and 1 microliter of M13 primer were reacted at 60° C. for 1 hour in 1.5 microliters of Klenow reaction buffer (0.1 M Tris HCl, pH 8.5, 50 mM $MgCl_2$) and 2.5 microliters of water (final volume = 10 microliters; this reaction is called annealing reaction). Subsequently, 1 microliter of Klenow DNA polymerase and 1 microliter of [α-$^{32}$P] dCTP were mixed with 10 microliters of the annealing reaction mixture. Then, 2.5 microliters of the mixture was put into red, blue, green and yellow microcentrifugal tubes and lightly mixed. Separately, four NTP mixtures (provisionally named A°, C°, G° and T°) shown in Table 1 were prepared. A°, C°, G° and T° were respectively added in an amount of 2.5 microliters to the red, blue, green and yellow tubes, followed by light mixing. The mixture in each tube was reacted at 20° C. for 15 minutes.

TABLE 1

| | NTP mixtures Amounts (microliters) | | | | |
|---|---|---|---|---|---|
| | 0.5 mM deoxy ATP | 0.5 mM deoxy GTP | 0.5 mM deoxy TTP | TE buffer | Others |
| A° | 1 | 20 | 20 | 20 | 61 of 0.07 mM dideoxy ATP |
| C° | 20 | 20 | 20 | 20 | 61 of 0.07 mM dideoxy CTP |
| G° | 20 | 1 | 20 | 20 | 61 of 0.07 mM dideoxy GTP |
| T° | 20 | 20 | 1 | 20 | 61 of 0.07 mM dideoxy TTP |

Fifteen minutes later, 0.5 mM dATP, 0.5 mM dCTP, 0.5 mM dGTP and 0.5 mM dTTP were added each in an amount of 2 microliters to the reaction mixture, and reacted at 20° C. for 15 minutes. After the reaction, 3 microliters of a formamide dye solution (formamide 100 ml, xylylene cyanol 0.1 g, bromophenol blue 0.1 g, 0.5 M EDTA 2 ml) was added to stop the reaction. The reaction mixture was then heat-treated for 3 minutes in boiling water, and subjected to electrophoresis on 6% polyacrylamide gel for 2 hours at 1500 V and 30 mA. The electrophoretic buffer solution used was TBE buffer solution (Tris base 10.8 g, boric acid 5.5 g, $Na_2$ $EDTA.H_2O$ 0.93 g/liter). After the electrophoresis, the gel was stripped off and immersed for 15 minutes in a gel fixing solution (methanol:acetic acid:water = 1:1:8 v/v). The fixing solution was removed as much as possible, and filter paper was layered on the gel to adhere the gel.

The back of that side of the gel to which the filter paper was applied was covered with a plastic wrap, and in a gel drying device (Atto AE-3700), the gel was fully dried, and then autoradiographed for 12-24 hours. The X-ray film was then developed and analyzed to determine the nucleotide sequence of pm525 HindIII-C.

By quite the same way as described above, the nucleotide sequences of pm411 HindIII-C and pm522 HindIII-C were determined. The results are shown in FIGS. 1 to 3.

The number of nucleotides of the DNA fragments of pm525 HindIII-C, pm411 HindIII-C and pm522 HindIII-C was 508 bp (base pairs), 511 bp and 451 bp, respectively.

(4) Isolation of pm525-enhancer DNA

The HindIII-C DNA fragment (0.5 microgram) of pm525 virus prepared by the method described in section 2) above was reacted with 2 units of HaeIII (a product of Takara Shuzo Co., Ltd.) at 37° C. for 1 hour in 20 microliters of a reaction buffer (10 mM Tris HCl, pH 7.5, 7 mM $MgCl_2$, 60 mM NaCl, 0.01 M dithiothreitol), and the reaction product was subjected to electroporesis at 50 mA for about 2 hours on 2% low-melting agarose gel (containing 0.5 microgram/ml of ethidium bromide). The presence of bands was determined by UV irradiation in a darkroom. A gel portion containing the band nearest to the cathode was sliced, and heated at 65° C. to melt the agarose. It was purified by the same method as described in section (2) above, and a 240 bp DNA segment having enhancer activity was isolated. That this DNA segment had enhancer activity was determined in Example 2 below. For the nucleotide sequence of this enhancer region, see the part surrounded by the dotted line in FIG. 3.

By quite the same method as above, pm411 enhancer DNA having a size of 243 bp and pm522 enhancer DNA having a size of 183 bp were isolated from the DNA fragments of pm411 HindIII-C and pm522 HindIII-C, respectively. For the nucleotide sequences of these enhancer regions, see the parts surrounded by the dotted lines in FIGS. 1 and 2.

EXAMPLE 2

This Example is for the purpose of assaying the enhancer activities of the enhancer DNA fragments prepared in Example 1. In this Example, the HindIII-C DNA fragments prepared in Example 1, (2) were used as such in order to demonstrate that they have enhancer activity independently of their orientation and position. It will be shown later that the isolated enhancer DNA segments have the same enhancer activity.

(1) Construction of recombinant plasmid DNA containing pm525 HindIII-C DNA fragment (1-1) Cleavage of pTK plasmid DNA with HindIII and dephosphorylation The plasmid pTK used in this experiment was obtained by cloning TK gene (thymidine kinase gene) obtained by cleavage of herpes simplex type-I viral DNA with the restriction endonuclease BamHI into the BamHI site of *E. coli* plasmid pBR322 (there are two types of plasmid pTK depending upon the direction of insertion; pTK and pTK). The TK DNA has no cleavage site for the restriction endonuclease SacI (the pTK plasmid used here was distributed by Prof. Hakura, Hospital attached to Institute of Micro-organism-Induced Diseases, Osaka University, Japan).

First, 2 micrograms of pTK DNA was cleaved with HindIII under the same conditions as in Example 1, (2), and then successively subjected to phenol treatment and ethanol precipitation. The resulting DNA was dissolved in 50 mM Tris buffer (pH 8.4), and 1 unit of alkaline phosphatase (a product of Takara Shuzo Co., Ltd.) was added. The reaction was carried out at 65° C. for 1 hour to perform dephosphorylation. Then, by the same method as in Example 1, (2), phenol treatment was carried out twice, and ethanol precipitation was carried out to obtain about 1.2 micrograms of DNA. It was dissolved in 30 microliters of distilled water.

(1-2) Insertion of pm525 HindIII-C DNA fragment into pTK plasmid DNA

Ten microliters (0.4 microgram) of the pm525 HindIII-C DNA fragment prepared in (1-1) and 5 microliters (0.2 microgram) of pTK plasmid DNA cleaved with HindIII were mixed, and reacted at 15° C. for 6 hours using 2 units of T4 DNA ligase in 20 microliters of a reaction buffer (30 mM Tris HCl, pH 7.8, 10 mM MgCl$_2$, 10 mM dithiothreitol, 0.5 mM ATP) to construct recombinant plasmids [FIG. 4, (E)].

Since there are two directions in which the HindIII-C DNA fragment is inserted into pTK, recombinant plasmids in which the HindIII-C DNA fragment was inserted in the two directions were selected, and used in the experiment of examining influences on transcriptional efficiency. The inserting direction will be more specifically explained below. The HindIII-C DNA fragment contained very small portions of the initiating sites of nucleotide sequences encoding $V_p$ and T-Ag (T antigen) which had existed in the original BK viral DNA. These portions were oriented in opposite directions to each other, and the HindIII-C DNA fragment was inserted so that either its Vp side or its T-Ag side was directed toward the TK DNA [see FIG. 5, (A) and (B)]. In FIG. 5, the long arrows near the plasmid DNA show the directions in which the plasmid DNA was to be read. With regard to the short arrows attached to the name of the recombinant plasmid, the arrow on C shows the direction in which Vp was to be read, and the arrow on TK shows the direction in which the TK DNA was to be read. For example, pBK525 HindIII-C.TK shows that the pm525 HindIII-C DNA fragment was inserted into the plasmid pBR322 so that its Vp side was oriented in the direction in which the TK DNA was to be read. C thus shows that the T-Ag side of the pm525 HindIII-C DNA fragment was oriented toward the TK DNA.

(1-3) Detection of transformants containing the recombinant plasmid for the purpose of infecting *E. coli* HB101 with the recombinant plasmid DNA The recombinant plasmid DNAs constructed in (1-2) were introduced into *E. coli* HB101 by the calcium chloride method in the same way as in Example 1, (3-1) to transform it, and the transformants were inoculated in a 1.4% agar medium (L-broth containing 25 micrograms/ml of ampicillin; to be described below). When they were cultivated at 37° C., colonies of HB101 which took up the plasmid DNA from outside were formed. To select transformants containing the desired plasmid DNA, some transformants were collected from each of the colonies by using sterilized toothpicks, inoculated in 1.5 ml of L-broth (bactotryptone 10 g, yeast extract 5 g, NaCl 5 g/liter, pH 7.2) containing 25 microgram/ml of ampicillin, and cultivated overnight at 37° C. with shaking. One milliliter of the culture fluid was then centrifuged at 12,000 rpm for 30 seconds. The pellets obtained were suspended in 500 microliters of a washing buffer (10 mM Tris.HCl, pH 8.0, lmM EDTA, 0.85% NaCl), and the suspension was centrifuged in the same way. The pellets were completely suspended in 7 microliters of STET liquor (50 mM Tris.HCl, pH 8.0, 8% sucrose, 5% Triton X-100, 50 mM EDTA). Then, 7 microliters of a lysozyme solution (10 mg/ml) dissolved in 30 mM Tris buffer (pH 8.0) was added in ice water to the suspension. They were mixed, and the mixture was immersed for 40 seconds in boiling water and immediately then, centrifuged at 12,000 rpm for 10 minutes. The pellets were then removed. The supernatant was mixed with 75 microliters of cold isopropanol. The mixture was left to stand at −20° C. for 10 minutes, and then centrifuged at 12,000 rpm for 7 minutes to precipitate DNA. The supernatant was removed as much as possible, and the DNA was dried under reduced pressure. The DNA was then digested with such restriction endonucleases as BamHI, HindIII and PvuII (products of Takara Shuzo Co., Ltd.), and subjected to agarose slab gel electrophoresis. Those transformants which contained the desired recombinant plasmid DNAs were selected on the basis of the number of DNA bands separated and the migration distances. Digestion with BamHI was carried out in a buffer consisting of 10 mM Tris HCl (pH 7.5), 10 mM MgCl₂, 50 mM NaCl and 1 mM dithiothreitol, and digetion with HindIII and PvuII, in a buffer consisting of 10 mM Tris HCl (pH 7.5), 6 mM MgCl₂, 60 mM NaCl and 1 mM dithiothreitol, by the same method as in Example 1,(2). The conditions for the electrophoresis were also in accordance with the method of Example 1, (2).

Figure 8:
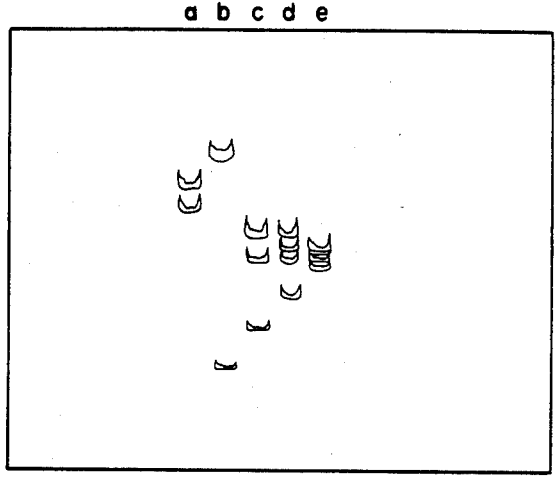

As a result of cleavage with BamHI, a band of the TK DNA appeared at a position of 3.6 kb, and a band of DNA resulting from the insertion of viral DNA fragment into pBR322, at a position of about 4.9 kb (FIG. 8, a). As a result of cleavage with HindIII, a band of viral DNA C fragment appeared at a position of about 0.5 kb, and a band of DNA resulting from the insertion of the TK DNA into pBR322, at a position of 7.9 kb (FIG. 8, b). pBR322 has one PvuII site; the TK DNA has two PvuII sites; and the C fragment (HindIII-C) of BK viral DNA has one PvuII site. When the DNA was cleaved with PvuII, the sizes of the DNAs resulting by cleavage differed according to the differences in the direction in which the TK DNA and the HindIII-C fragment DNA were inserted into pBR322 [FIG. 5, (A), (B) and (C)]. Hence, by examining the sizes of the DNAs formed by cleavage with PvuII by agarose gel electrophoresis, the orientations of the inserted DNAs could be determined. In FIG. 5, (A), cleavage with PvuII gave bands having a size of 2.8, 2.7, 2.0 and 0.9 kb. In FIG. 8, (C) and FIG. 5 (B), cleavage with PvuII gave bands having a size of 2.7, 2.3, 2.0 and 1.4 kb. In FIG. 8, (C) and FIG. 5, (C), bands having a size of 2.3, 2.26, 2.0 and 1.8 kb were formed by cleavage with PvuII.

Transformants containing the desired recombinant plasmid DNAs (provisionally named pBK525 HindIII-$\overrightarrow{C}$.$\overrightarrow{TK}$, pBK525 HindIII-$\overleftarrow{C}$.$\overrightarrow{TK}$ and pBK525 HindIII-$\overleftarrow{C}$.$\overrightarrow{TK}$; see FIG. 5, A, B and C) could thus be selected on the basis of the number and sizes of the DNA fragments formed by cleavage with BamHI, HindIII and PvuII.

By the same methods as described in (1-1) to (1-3), recombinant plasmids containing pm411 HindIII-C and pm522 HindIII-C DNA fragments (provisionally named pBK411 HindIII-$\overrightarrow{C}$.$\overrightarrow{TK}$, pBK411 HindIII-$\overleftarrow{C}$.$\overrightarrow{TK}$ and pBK411 HindIII-$\overleftarrow{C}$.$\overrightarrow{TK}$, and pBK522 HindIII-$\overrightarrow{C}$.$\overrightarrow{TK}$, pBK522 HindIII-$\overleftarrow{C}$.$\overrightarrow{TK}$ and pBK522 HindIII-C.TK) were constructed [see FIG. 6, (A), (B) and (C), and FIG. 7, (A), (B) and (C)].

(1-4) Purification of recombinant plasmid DNAs used in experiments for introduction of DNA into cultivated cells The recombinant plasmid DNAs used for introduction into cultivated cells were prepared by a density gradient ultracentrifugation method using cesium chloride containing ethidium bromide (T. Maniatis, F. F. Fritsch and J. Sambrook: Molecular Cloning, p. 86, Cold Spring Harbour Lab., 1982).

(2) Introduction of the recombinant DNAs into mouse L(TK⁻) cells and their expression Mouse fibroblast cells L(TK⁻) were used as recipient cells. These cells are a thymidine kinase-deficient strain (TK⁻), and cannot grow if their thymidylate synthase is inhibited with aminopterin. If they take up TK DNA from outside, they synthesize thymidine-1-phosphoric acid → thymidine-3-phosphoric acid from thymidine in the culture broth by a salvage pathway, and can grow even in the presence of aminopterin. Hence, by cultivating the above cells in HAT medium (Eagle's MEM containing 15 micrograms/ml of hypoxanthine, 0.18 microgram/ml of aminopterin, 5 micrograms/ml of thymidine and 10% calf serum), cells which have taken up a plasmid DNA containing foreign TK DNA can be selected. Specifically, the following procedure was taken.

Twenty-four hours before the transfection, the cells were prepared at a rate of 2.5–5.0×10⁵ for each plate having a diameter of 60 mm using Eagle's MEM containing 10% of calf serum. Three to five hours before the transfection, the medium was replaced by a fresh supply of the same culture medium. One microgram of the DNA per plate was cleaved at a site which did not affect the expression of the TK gene and the enhancer to form linear DNA, and transfected. No carrier DNA was used. SalI or SacI (both the products of Takara Shuzo Co., Ltd.) was used as the restriction endonuclease. With SalI, the same conditions as in Example 1 were used. With SacI, a buffer consisting of 6 mM Tris HCl (pH 7.4), 6.0 mM MgCl₂, 20 mM NaCl and 1 mM dithiothreitol was used, and otherwise, the same conditions as in Example 1 were employed.

The introduction experiment was carried out by using the following recombinant plasmids.

(a) A recombinant plasmid constructed by inserting only the HindIII-C DNA fragment of viral DNA into pBR322, followed by cleavage with SalI. Since no colony formed with this plasmid, the data are omitted in this application. (Negative control)

Figure 9:
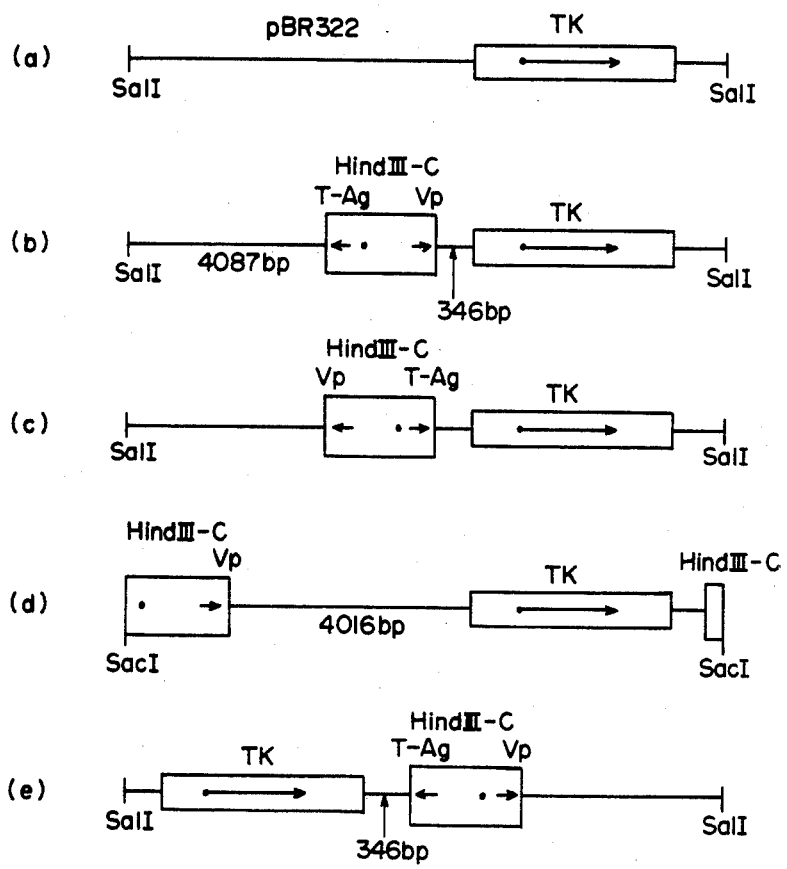

(b) A recombinant plasmid constructed by inserting only the TK gene into pBR322, followed by cleavage with SalI [FIG. 9, (a)].

(c) A recombinant plasmid constructed by inserting TK gene and HindIII-C DNA fragment into pBR322 so that the HindIII-C DNA fragment was located immediately upstream of TK gene with its Vp side directed toward TK gene, followed by cleavage with SalI [FIG. 9, (b)].

(d) A recombinant plasmid constructed by inserting the same DNAs as in (c) into pBR322 so that the HindIII-C DNA fragment was located immediately upstream of TK gene with its T-Ag side directed toward TK gene, followed by cleavage with SalI [FIG. 9, (c)].

(e) A recombinant plasmid constructed by inserting the same DNAs as in (c) above so that the HindIII-C DNA fragment was located 4kb upstream of TK gene with its Vp side directed toward TK gene, followed by cleavage with SacI [FIG. 9, (d)].

(f) A recombinant plasmid constructed by inserting the same DNAs as in (c) above so that the HindIII-C DNA fragment was located downstream of TK gene, followed by cleavage with SalI [FIG. 9, (e)].

Each of the plasmid DNAs was introduced into the cultivated cells by the method of Wigler et al. (M. Wigler, S. Silverstein, L. S. Lee, A. Pellicer, T. C. Cheng, and R. Axel: Cell, 11, 223, 1977) to transfect them. Specifically, 31 microliters of 2M CaCl₂ was mixed with 1 microgram of the plasmid DNA dissolved in 250 microliters of distilled water. To the mixture was gradually added dropwise 250 microliters of HBS solution (NaCl 1.636 g, Hepes 1.19 g, Na₂HPO₄ 0.04 g/ 100 ml, adjusted to pH 7.10 with 1N NaOH). The mixture was left to stand at room temperature for 15 minutes, and then sprinkled over the entire surface of the cultivated cells. The cells were then cultivated at 37° C. Four hours later, the liquid was removed, and the residue was washed with Eagle's MEM medium, and then reated with 1.5 ml of a 15% glycerol solution (glycerol 15 ml, 2×HBS solution 50 ml, H₂O 35 ml) for 1 to 1.5 minutes. Then, the liquid was removed as much as possible. The residue as again washed, and then cultivated in Eagle's MEM containing 10% calf serum. Two days after the transfection, the cells were peeled off with trypsine, and one plate was again cultivated dividedly in three plates. At the same time, the medium was replaced by HAT medium. The HAT medium was exchanged every 1 to 2 days and the cultivation was continued. Approximately on the fifth day, colonies of TK cells began to form. Two weeks after the transfection, the plates were stained by the Giemsa staining method, and the number of colonies was counted. The activity of the enhancer was indicated as a specific activity with respect to the activity of pTK which is taken as 1.

As a result, the HindIII-C DNA fragments of pm411, pm522 and pm525 viral DNAs showed 10.1 to 20.0 times as high a transcription enhancing activity as the control in the mouse L TK− cells [Table 2, (a), (b), (c), (d) and (e)].

This activity was exhibited irrespective of the orientation of the HindIII-C DNA fragment [Table 2, (b) and (c)].

Furthermore, the enhancer DNA 4 kb apart from the target DNA showed an enhancer activity about 70% of that of the enhancer located near the target DNA [Table 2, (b) and (d)]. Even when positioned downstream of the target gene, the enhancer DNA showed an enhancer activity 3.0 times as high as that of the control.

TABLE 2

| | Recombinant plasmid | Specific activity |
|---|---|---|
| a | p TK⟶/SalI | 1 |
| b | pBK501 HindIII-C⟶. TK⟶/SalI | 6.7 |
| | pBK411 HindIII-C⟶. TK⟶/SalI | 18.7 |
| | pBK522 HindIII-C⟶. TK⟶/SalI | 10.7 |
| | pBK525 HindIII-C⟶. TK⟶/SalI | 19.3 |
| c | pBK501 HindIII-⟵C. TK⟶/SalI | 4.3 |
| | pBK411 HindIII-⟵C. TK⟶/SalI | 10.1 |
| | pBK522 HindIII-⟵C. TK⟶/SalI | 16.0 |
| | pBK525 HindIII-⟵C. TK⟶/SalI | 20.0 |
| d | pBK501 HindIII-⟵C.⟵TK/SacI | 4.8 |
| | pBK411 HindIII-⟵C.⟵TK/SacI | 13.5 |
| | pBK522 HindIII-⟵C.⟵TK/SacI | 8.0 |
| | pBK525 HindIII-⟵C.⟵TK/SacI | 14.1 |
| e | pBK501 HindIII-⟵C.⟵TK/SalI | 1.6 |
| | pBK411 HindIII-⟵C.⟵TK/SalI | 4.3 |
| | pBK522 HindIII-⟵C.⟵TK/SalI | 3.0 |
| | pBK525 HindIII-⟵C.⟵TK/SalI | 4.6 | pBK501 HindIII-C in the above table is a recombinant plasmid DNA contructed from wild type BKV, WT 501 strain in the same way as in the foregoing Examples.

EXAMPLE 3

(1) Contruction of recombinant plasmid DNAs containing enhancer DNA segments (1-1) Linking of HindIII linker with the enhancer DNA segment One microgram of a phosphorylated HindIII linker (a product of Takara Shuzo Co., Ltd.) was added to 0.4 microgram of an enhancer DNA fragment isolated as in Example 1, (4). The mixture was reacted with 1 unit of T4 DNA ligase at 22° C. for 6 hours in 20 microliters of a buffer consisting of 66 mM Tris HCl (pH 7.6), 1 mM ATP, 1 mM spermidine, 10 mM MgCl₂, 15 mM dithiothreitol, bovine serum albumin 0.2 mg/ml). The reaction mixture was treated with phenol and then precipitated with ethanol to obtain a DNA fragment having the linker. It was digested with HindIII, and then purified by phenol treatment and ethanol precipitation in the same way as above.

(1-2) Insertion of the enhancer DNA segment into the HindIII site of pTK plasmid DNA Ten microliters (0.4 microgram) of the pTK plasmid prepared as above (cleaved with HindIII and dephosphorylated) prepared in (1-1) was mixed with the enhancer DNA segment modified so as to have a HindIII terminus (obtained in (1-1) above), and by the same procedure as described in Example 2, (1-2) and (1-3), the enhancer DNA segment was inserted into the HindIII site of pTK plasmid DNA. *E. coli* HB101 was then transfected with the plasmid. The transformants were cultivated at 37° C. in a 1.4% agar medium containing 25 micrograms/ml of ampicillin. DNAs were extracted from the resulting colonies in the same way as in Example 2, (1-3) and digested with HindIII. The desired recombinant plasmid DNAs were selected by electrophoresis.

(2) Transfection and expression of the recombinant plasmids in mouse L (TK−) cells In the same way as in Example 2, (2), the recombinant plasmids containing enhancer DNAs obtained in (1) above were each introduced into mouse L(TK−) cells to transfect them, and their function was examined. The results are shown in Table 3.

TABLE 3

| | Recombinant plasmid | Specific activity |
|---|---|---|
| a | p TK→/SalI | 1 |
| b | pBK501-enhancer. TK→/SalI | 6.0 |
| | | 14.2 |
| | pBK411-enhancer. TK→/SalI | |
| | | 15.4 |
| | pBK522-enhancer. TK→/SalI | |
| | | 18.5 |
| | pBK525-enhancer. TK→/SalI | |

The foregoing results clearly demonstrate that the enhancer DNA segments of this invention have a very good activity of enhancing the level of transcription of incorporated genes in cells.

What is claimed is:

1. An enhancer DNA segment having an excellent action of enhancing the transcriptional efficiency of an incorporated gene in a cell, said segment being within the HindIII-C segment of and derived from a human papovavirus BK mutant designated as pm411, pm522 or pm525 and having a size of 243 bp, 183 bp and 240 bp, respectively.

2. The enhancer DNA segment of claim 1 which is derived from the human papovavirus BK mutant pm411 and has the following nucleotide sequence

| CCT | TTG | TCC | AGT | TTA | ACT | ATT | AAC | TGC | CAC | TGG | CTG |
|---|---|---|---|---|---|---|---|---|---|---|---|
| GCT | GCC | CAG | TCA | TGC | ACT | TTC | CTT | CCT | GAG | GTC | ATG |
| GCT | GGC | TGC | CCA | GTC | ATG | CAC | TTT | CCT | TCC | TGA | GGG |
| CTG | CCC | AGT | CAT | GCT | GAG | GTC | ATG | GCT | GGC | TGC | CCA |
| GTC | ATG | CAC | TTT | CCT | TCC | TGA | GGG | CTG | CCC | AGT | CAT |
| GCA | CTT | TCC | TTC | CTG | AGG | TCA | TGG | TTT | GGC | TGC | ATT |
| CCA | TGG | GTA | AGC | AGC | TCC | TCC | CTG | TGG. | | | |

3. The enhancer DNA segment of claim 1 which is derived from the human papovavirus BK mutant pm522 and has the following nucleotide sequence

| CCT | TTG | TCC | AGT | TTA | ACT | ATT | AAC | TGC | CAC | TGG | CTG |
|---|---|---|---|---|---|---|---|---|---|---|---|
| GCT | GCC | CAG | TCA | TGC | ACT | TTC | CTT | CCT | GAG | GTC | ATG |
| GCT | GGC | TGC | CCA | GTC | ATG | CAC | TTT | CCT | TCC | TGA | GGG |
| CTG | CCC | AGT | CAT | GCA | CTT | TCC | TTC | CTG | AGG | TCA | TGG |
| TTT | GGC | TGC | ATT | CCA | TGG | GTA | AGC | AGC | TCC | TCC | CTG |
| TGG. | | | | | | | | | | | |

4. The enhancer DNA segment of claim 1 which is derived from the human papovavirus BK mutant pm 525 and has the following nucleotide sequence

| CCT | TTG | TCC | AGT | TTA | ACT | ATT | AAC | TGC | CAC | TGG | CTG |
|---|---|---|---|---|---|---|---|---|---|---|---|
| GCT | GCC | CAG | TCA | TGC | ACT | TTC | CTT | CCT | GAG | GTC | ATG |
| GCT | GGC | TGC | CCA | GTC | ATG | CAC | TTT | CCT | TTG | TCC | AGT |
| TTA | ACT | ATT | AAC | TGC | CAC | TGG | CTG | GCT | GCC | CTA | GTC |
| ATG | CAC | TTT | CCT | TCC | TGA | GGG | CTG | CCT | AGT | CAT | GCA |
| CTT | TCC | TTC | CTG | AGG | TCA | TGG | TTT | GGC | TGC | ATT | CCA |
| TGG | GTA | AGC | AGC | TCC | TCC | CTG | TGG. | | | | |

5. A process for enhancing the expression of a gene encoding a biologically active substance in host eukaryotic cells, which comprises introducing the enhancer DNA of claim 1 into a vector DNA containing the gene encoding the biologically active substance, transforming the host eukaryotic cells with the resulting recombinant DNA, and cultivating the transformed cells.

* * * * *